US009056882B2

(12) United States Patent
Indukuri et al.

(10) Patent No.: US 9,056,882 B2
(45) Date of Patent: Jun. 16, 2015

(54) PROCESS FOR THE PREPARATION OF TENOFOVIR

(71) Applicants: Venkata Sunil Kumar Indukuri, Hyderabad (IN); Sree Rambabu Joga, Hyderabad (IN); Seeta Ramanjaneyulu Gorantla, Hyderabad (IN); Satyanarayana Chava, Hyderabad (IN)

(72) Inventors: Venkata Sunil Kumar Indukuri, Hyderabad (IN); Sree Rambabu Joga, Hyderabad (IN); Seeta Ramanjaneyulu Gorantla, Hyderabad (IN); Satyanarayana Chava, Hyderabad (IN)

(73) Assignee: Laurus Labs Private Ltd., Hyderabad (IN)

( * ) Notice: Subject to any disclaimer, the term of this patent is extended or adjusted under 35 U.S.C. 154(b) by 0 days.

(21) Appl. No.: 14/356,609

(22) PCT Filed: Nov. 15, 2012

(86) PCT No.: PCT/IB2012/002362
§ 371 (c)(1),
(2) Date: May 7, 2014

(87) PCT Pub. No.: WO2013/072745
PCT Pub. Date: May 23, 2013

(65) Prior Publication Data
US 2014/0303368 A1    Oct. 9, 2014

(30) Foreign Application Priority Data

Nov. 16, 2011 (IN) .......................... 3930/CHE/2011

(51) Int. Cl.
*A61K 31/675* (2006.01)
*C07F 9/6561* (2006.01)

(52) U.S. Cl.
CPC ........... *C07F 9/65616* (2013.01); *A61K 31/675* (2013.01)

(58) Field of Classification Search
CPC ........................ A61K 31/675; C07F 9/65616
See application file for complete search history.

(56) References Cited

U.S. PATENT DOCUMENTS

| 5,733,788 A |  | 3/1998 | Bischofberger |
|---|---|---|---|
| 5,922,695 A | * | 7/1999 | Arimilli et al. ................. 514/81 |
| 6,465,649 B1 |  | 10/2002 | Gutierrez et al. |
| 8,049,009 B2 |  | 11/2011 | Vasireddy et al. |

FOREIGN PATENT DOCUMENTS

| CN | 101906119 A | 12/2010 |
|---|---|---|
| CN | 102060876 A | 5/2011 |
| WO | 9403467 A2 | 2/1994 |

* cited by examiner

*Primary Examiner* — Erich A Leeser
(74) *Attorney, Agent, or Firm* — Blank Rome LLP

(57) ABSTRACT

The present invention provides a process for preparation of tenofovir by dealkylation of its phosphonate ester using Ionic complexes. The present invention also provides a process for preparation of tenofovir disoproxil or a salt thereof using the tenofovir of the present invention.

20 Claims, No Drawings

PROCESS FOR THE PREPARATION OF TENOFOVIR

PRIORITY

This application is a U.S. National Phase of PCT/IB2012/002362, filed Nov. 15, 2012, which claims the benefit under Indian Provisional Application No. 3930/CHE/2011, filed Nov. 16, 2011, the content of each of which is incorporated by reference herein.

FIELD OF THE INVENTION

The present invention generally relates to a process for preparation of Tenofovir by dealkylation of its phosphonate ester using Ionic complexes, a process for its conversion into Tenofovir disoproxil and its pharmaceutically acceptable salts, and pharmaceutical compositions containing the same.

BACKGROUND OF THE INVENTION

Tenofovir, also known as 9-[2-(R)-(phosphonomethoxy)propyl]adenine (PMPA), is represented by the following structure of Formula I:

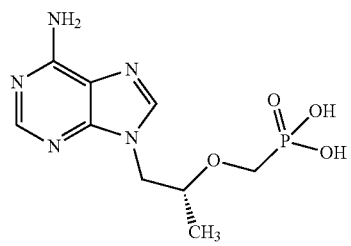

Tenofovir is approved for commercial use as in the form of Tenofovir disoproxil fumaric acid salt, chemically known as 9-[(R)-2-[[bis[[(isopropoxycarbonyl) oxy]methoxy]phosphinyl]methoxy]propyl]adenine fumarate, is represented by the following structure of Formula:

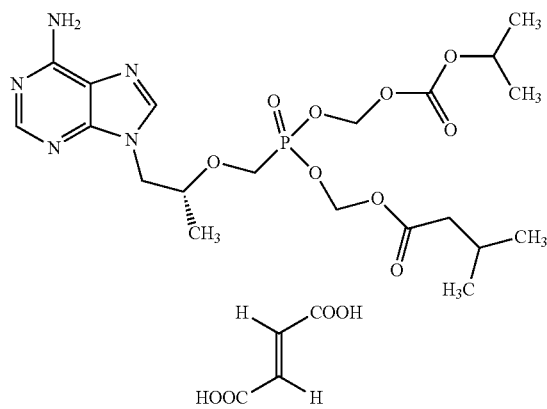

Tenofovir disoproxil fumarate is a highly potent antiviral agent and is available in the market under the brand name VIREAD® in the form of 300 mg of oral tablets and in combination with other antiviral agents.

Patent publication WO 94/03467 ("the '467 publication") and U.S. Pat. No. 5,733,788 ("the '788 patent") discloses a process for preparation of tenofovir by reaction of 9-[2-(R)-hydroxypropyl) adenine with di-(2-alkyl)-p-toluenesulfonyloxy methyl phosphonate in presence of strong bases such as sodium hydride, lithium hydridein dimethyl formamide followed by dealkylation with bromotrimethyl silane in Acetonitrile. The process disclosed in the '788 patent is schematically represented as follows:

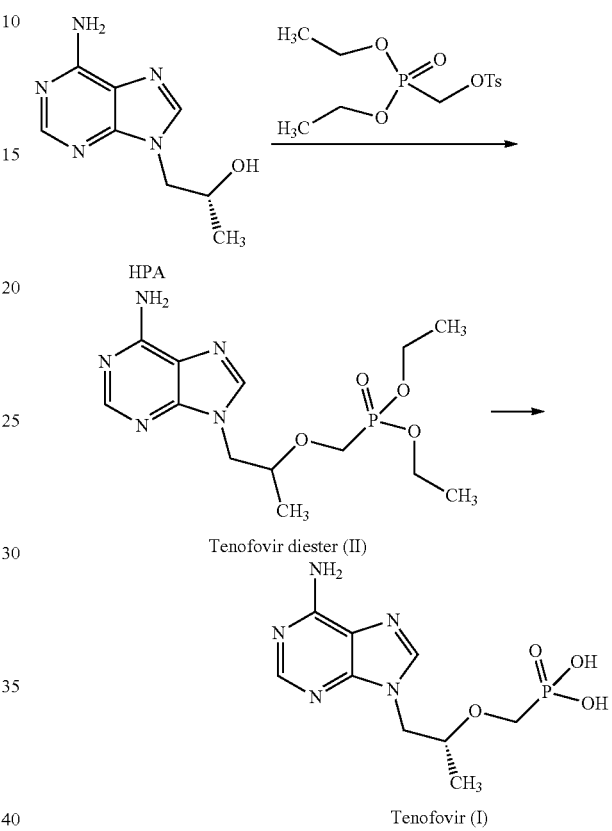

U.S. Pat. No. 5,922,695 ("the '695 patent") discloses a process for preparation of tenofovir by reaction of 9-[2-(R)-hydroxy propyl)adenine with diethyl-p-toluenesulfonyloxy methyl phosphonate in presence of Lithium tert-butoxide in Tetrahydrofuran followed by dealkylation with bromotrimethylsilane in Acetonitrile.

U.S. Pat. No. 6,465,649 ("the '649 patent") discloses a process for preparation of tenofovir by dealkylation of 9-[2-(R)-(diethyl phosphonomethoxy)propyl]adenine with chlorotrimethylsilane in chlorobenzene.

The '649 patent further described conventional methods for dealkylating phosphonate esters include reaction with aqueous solutions of concentrated HCl or HBr are inappropriate as many of the functional groups on the phosphonates are acid labile, which cannot tolerate these harsh acidic conditions for instance amino group as in the case of tenofovir is readily converted into keto compound (Hypoxanthine impurity) under these concentrated acidic conditions.

The '649 patent also mentions that chlorotrimethylsilane is less reactive and can be used only for the deprotection of the more labile phosphonate esters for example dimethyl phosphonate esters. The deprotection of diethyl phosphonate ester requires long reaction times resulting in unsatisfactory yields. In order to overcome this problem, the use of an activating agent like sodium or lithium iodide to the reaction medium results in faster reaction times. However, the use of such salts leads to metal contamination of the final product and thus additional process steps such as solvent crystallization required to remove.

Moreover, the use of halo trimethylsilanes such as bromo and chlorotrimethylsilanes described in the aforementioned literature for dealkylation reaction are moisture sensitive, expensive and requires special handling procedures due to its highly corrosive in nature, particularly on commercial scale and thus require more care to use; which in turn result to an increase in the manufacturing cost.

U.S. Pat. No. 8,049,009 ("the '009 patent") discloses a process for preparation of tenofovir by reaction of 9-[2-(R)-hydroxypropyl) adenine with diethyl-p-toluenesulfonyloxy methyl phosphonate in presence of Magnesium tert-butoxide in dimethyl formamide followed by dealkylation with an acid such as aqueous HBr, aqueous HCl, HBr in acetic acid and HCl gas in isopropyl alcohol.

The literature mentioned above for instance "the '009 patent further discloses" isolation of the intermediate compound phosphonate diester, prior to the dealkylation is performed by complete removal of the dimethyl formamide from the reaction medium. Removal of the high boiling solvent dimethyl formamide from the reaction mixture would require prolonged period of time at higher temperature, this leads to degradation of the low melting phosphonate diester product. Accordingly, extensive purification procedures are required in order to obtain the necessary quality of the end product and results low product yield thereby making the process quite expensive.

It would be desirable to provide a process for the preparation of tenofovir, which is simple and cost effective; and a process for its use thereof in the preparation of tenofovir disoproxil fumarate in a convenient, cost efficient manner and on a commercial scale.

The present invention provides a process for preparation of tenofovir using suitable dealkylating Ionic complexes that are away from the aforementioned difficulties such as moisture sensitive, corrosive and expensive dealkylating reagents and avoids additional process steps like solvent distillation to minimize the product degradation. The process of the present invention can be practiced on an industrial scale, and also can be carried out without sacrifice of overall yield.

OBJECT OF THE INVENTION

The main object of the invention is to provide a simple, cost effective process for dealkylation of phosphonate esters of high purity without the formation of undesired impurities.

Another object of the invention is to provide a process for preparation of tenofovir in high yield and purity by dealkylation of phosphonate esters using less expensive dealkylating agents.

Yet another object of the invention is to provide a process for preparation of tenofovir in high yield and purity without involving the prolonged distillation steps at higher temperatures, thereby substantially minimize the product degradation.

Further object of the invention is to use dealkylating ionic complexes for dealkylation of phosphonate esters, which are less corrosive and safe to use on an industrial scale.

SUMMARY OF THE INVENTION

The present invention encompasses a process for preparation of tenofovir and its conversion into tenofovir disoproxil or a pharmaceutically acceptable salt thereof with high product yield and quality.

In accordance with one embodiment, the present invention provides a process for preparation of tenofovir, comprising: dealkylating (R)-9-[2-(di-Alk-phosphono methoxy) propyl] adenine of Formula II with a suitable dealkylating Ionic complex;

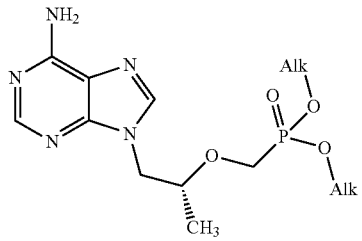

Formula II wherein the "Alk" represents $C_{1-4}$ alkyl; and suitable dealkylating Ionic complex is selected from the group comprising a complex of amide and an acid, a complex of aluminium salt and an amide-acid reagent and a complex of aluminium salt and an amine.

In accordance with a second embodiment, the present invention provides a process for preparation of tenofovir, comprising: dealkylating (R)-9-[2-(diethylphosphono methoxy)propyl]adenine of Formula II with a suitable dealkylating Ionic complex;

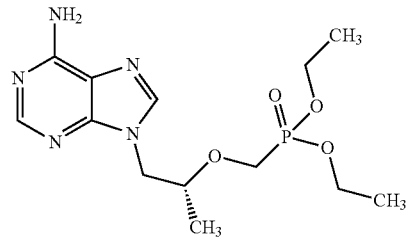

Formula II wherein the suitable dealkylating Ionic complex is selected from the group comprising a complex of amide and an acid, a complex of aluminium salt and an amide-acid reagent and a complex of aluminium salt and an amine.

In accordance with a third embodiment, the present invention provides a process for preparation of tenofovir, comprising: dealkylating (R)-9-[2-(diethylphosphono methoxy) propyl]adenine of Formula II with a suitable dealkylating Ionic complex, wherein the suitable dealkylating Ionic complex is a complex of amide and an acid.

In accordance with a fourth embodiment, the present invention provides a process for preparation of tenofovir, comprising: dealkylating (R)-9-[2-(diethylphosphono methoxy) propyl]adenine of Formula II with a suitable dealkylating Ionic complex, wherein the suitable dealkylating Ionic complex is a complex of aluminum salt and an amide-acid reagent.

In accordance with a fifth embodiment, the present invention provides a process for preparation of tenofovir, comprising: dealkylating (R)-9-[2-(diethylphosphono methoxy) propyl]adenine of Formula II with a suitable dealkylating Ionic complex, wherein the suitable dealkylating Ionic complex is a complex of aluminum salt and an amine.

In accordance with a sixth embodiment, the present invention provides a process for preparing tenofovir disoproxil or a pharmaceutically acceptable salt thereof, comprising:

a) dealkylating the (R)-9-[2-(di-Alk-phosphono methoxy)propyl]adenine of Formula II as processes herein described above to obtain tenofovir, and
b) converting the resultant tenofovir into tenofovir disoproxil or a pharmaceutically acceptable salt thereof.

In accordance with a seventh embodiment, the present invention provides a pharmaceutical composition comprising a therapeutically effective amount of tenofovir disoproxil or a pharmaceutically acceptable salt thereof prepared by the processes of the present invention and at least one pharmaceutically acceptable carrier.

DETAILED DESCRIPTION OF THE INVENTION

The present invention provides an improved process for the preparation of tenofovir. In particular, the present invention provides a process to prepare tenofovir by using safe and simple inexpensive dealkylating agents in the dealkylation of (R)-9-[2-(di-alkyl-phosphonomethoxy)propyl]adenine of Formula II (phosphonate ester). The present invention further provides a process for preparing tenofovir disoproxil or a pharmaceutically acceptable salt thereof from the tenofovir obtained from the process of the present invention.

In one embodiment, the present invention provides a process for preparing tenofovir, comprising: dealkylating (R)-9-[2-(di-Alk-phosphono methoxy)propyl]adenine of Formula II with a suitable dealkylating Ionic complex;

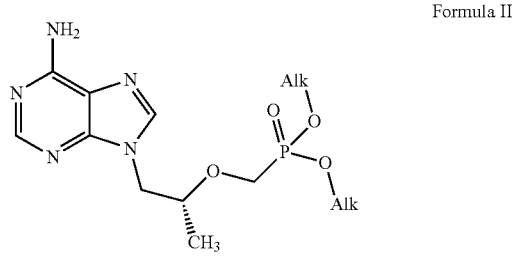

Formula II wherein the "Alk" represents $C_{1-4}$ alkyl, preferably ethyl; and suitable dealkylating Ionic complex is selected from the group comprising a complex of amide and an acid, a complex of aluminium salt and an amide-acid reagent and a complex of aluminium salt and an amine.

In a preferred embodiment, the present invention provides a process for preparing tenofovir, comprising: dealkylating (R)-9-[2-(diethylphosphono methoxy)propyl]adenine of Formula II with a suitable dealkylating Ionic complex; wherein the suitable dealkylating Ionic complex is selected from the group comprising a complex of amide and an acid, a complex of aluminium salt and an amide-acid reagent and a complex of aluminium salt and an amine.

The starting material (R)-9-[2-(diethylphosphono methoxy)propyl]adenine of Formula II is known in the art and can be prepared by any known method, for example starting compound of Formula II may be synthesized as disclosed in U.S. Pat. No. 5,733,788.

Alternatively, the (R)-9-[2-(diethylphosphono methoxy)propyl]adenine of Formula II can be prepared by reacting 9-[2-(R)-(hydroxy)propyl]adenine (HPA) with diethyl-p-toluene sulfonyloxy methyl phosphonate in presence of magnesium tert-butoxide or combination of sodium amide and magnesium chloride in an organic solvent such as dimethyl formamide and the like to obtain (R)-9-[2-(diethylphosphono methoxy)propyl]adenine of Formula II. The resultant (R)-9-[2-(diethyl-phosphono methoxy)propyl]adenine is used as such without involving tedious workup procedure like solvent distillation at high temperature, for the preparation of tenofovir.

In a preferred embodiment, the present invention provides a process for preparing tenofovir, comprising: dealkylating (R)-9-[2-(diethylphosphono methoxy)propyl]adenine of Formula II with a complex of amide and an acid.

The amide in the foregoing process may be selected from the group consisting of dimethyl formamide, dimethyl acetamide, formamide, N-methyl formamide, methyl formamide, 2-pyrrolidone, N-Methyl-2-pyrrolidone, N-vinyl pyrrolidone and the like and mixtures thereof; preferably dimethyl formamide.

The acid in the foregoing process may be selected from the group consisting of hydrochloric acid, hydrobromic acid, orthophosphoric acid, sulfuric acid and the like and mixtures thereof; preferably hydrochloric acid. The acid may be in the form of an aqueous, anhydrous or gas form.

Preferably the complex of amide and an acid is a complex of dimethyl formamide (DMF) and hydrochloric acid (HCl).

The complex of amide and an acid in any ratio can be prepared by mixing an acid and amide, as prepared by methods known in the art, for example DMF and HCl forms a complex of DMF.HCl. The complex nature was characterized as disclosed in the prior literature, for example Russian Chemical Bulletin, Vol. 42, No. 9, September 1993 and Kinetics and Catalysis Volume 43, Number 5, 671-674, the content of which are incorporated herein by reference.

The complex of amide and an acid can be prepared either by amide may be taken separately and mixed it with an acid and then resultant complex of amide and an acid may be added into the compound of Formula II or an acid may be mixed with an amide obtaining an existing solution from a previous processing step containing compound of Formula II. The sequence of addition of amide and/or an acid is not particularly critical.

The molar ratio of the amide: acid used in the process according to the invention may vary between 1:0.5 and 1:3.

In another preferred embodiment, the present invention provides a process for preparing tenofovir, comprising: dealkylating (R)-9-[2-(diethylphosphono methoxy)propyl]adenine of Formula II with a complex of aluminium salt and an amide-acid reagent.

The complex of aluminium salt and an amide-acid reagent may be prepared by mixing a complex of an amide-acid reagent prepared as described above and an aluminium salt at ambient temperature. Further, the complex may be formed either by first preparing amide-acid reagent as process described above and mixed it with aluminium salt and then resultant complex is added into the compound of Formula II or an acid and aluminium salt may be mixed with an amide obtaining an existing solution from a previous processing step containing compound of Formula II.

The aluminium salt in the foregoing process may be selected from the group consisting of aluminium halide such as aluminium chloride, aluminium bromide aluminium iodide and the like and mixtures thereof; preferably the aluminium salt is aluminium chloride.

In one embodiment, the complex of aluminium salt and an amide-acid reagent is a complex of aluminium salt and DMF-.HCl.

In another preferred embodiment, the present invention provides a process for preparing tenofovir, comprising: dealkylating (R)-9-[2-(diethylphosphono methoxy)propyl]adenine of Formula II with a complex of aluminium salt and an amine.

The complex of aluminium salt and an amine can be prepared by mixing an amine and an aluminium salt, defined as above at ambient temperature.

The aluminium salt and the amine can be introduced in any order, for example the aluminium salt is added to the amine and then the compound of Formula II is introduced or the compound of formula II is added to the amine and then the aluminium salt is introduced. The sequence of addition of aluminium salt and/or amine is not particularly critical. Alternatively, the aluminium salt-amine reagent is formed beforehand and is optionally isolated, before the introduction of the compound of Formula II.

The amine in the foregoing process may be selected from a compound of formula $(R)_2NH$, in which R represents a linear or branched $C_1-C_4$ alkyl group, a linear or branched $C_2-C_6$ alkenyl group, a $C_3-C_7$ cycloalkyl group, an aryl group or an aralkyl group; a compound of Formula NRaRbRc, in which Ra, Rb and Rc independently represents hydrogen, an aryl group or a linear or branched $C_1-C_4$ alkyl group, or Ra, Rb or Rc may form a cyclic ring with the nitrogen. The amine may be in the form of its free amine or its acceptable salt form for example hydrochloride salt.

The linear or branched $C_1-C_4$ alkyl group includes, but is not limited to methyl, ethyl, propyl, isopropyl, butyl, isobutyl, sec-butyl, or tert-butyl group and the like; the linear or branched $C_2-C_6$ alkenyl group includes, but is not limited to an ethenyl or vinyl, propenyl or allyl, 1-propenyl, n-butenyl, isobutenyl, 3-methylbut-2-enyl, n-pentenyl or hexenyl group and the like; the $C_3-C_7$ cycloalkyl includes, but is not limited to cyclopropyl, cyclohexyl and the like; an aryl group includes, but is not limited to phenyl, naphthyl and the like; an aralkyl group includes, but is not limited to benzyl, 1-phenylethyl and the like.

Preferably, the amine can be selected from the group consisting of diethylamine, diisopropyl amine, di-n-propylamine, diallylamine, diphenylamine, dibenzylamine, trimethylamine, triethylamine, tripropylamine, tributylamine, N,N-dimethylethylamine, N,N-diethylmethylamine, N,N-dimethylbutylamine, N,N-dimethylaniline, N,N-diethylaniline, N-methyl-N-ethyl aniline, N-methyl-N-isopropyl aniline, 1-N,N-dimethylnaphthalene, 2-N,N-dimethyl naphthalene, dicyclopropylamine, dicyclohexylamine, pyridine, 2,6-lutidine and the like and mixtures thereof.

Preferably, the complex of aluminium salt and an amine can be selected for the group consisting of aluminium chloride-trimethylamine. HCl, aluminium chloride-diisopropylamine, aluminium chloride-diethylamine and aluminium chloride-2,6-lutidine.

The dealkylation of (R)-9-[2-(diethyl-phosphono methoxy)propyl]adenine of Formula II may be carried out in a suitable solvent. The suitable solvent includes, but is not limited to amides such as dimethyl formamide, dimethyl acetamide, formamide, N-methyl formamide, methyl formamide, 2-pyrrolidone, N-Methyl-2-pyrrolidone, N-vinyl pyrrolidone and the like; sulfoxides such as dimethyl sulfoxide and the like; and mixtures thereof; preferably dimethyl formamide, N-Methyl-2-pyrrolidone or dimethyl sulfoxide.

The dealkylation of (R)-9-[2-(diethyl-phosphono methoxy)propyl]adenine of Formula II may be carried out at a temperature of about ambient temperature to about reflux temperature for about 3 to 10 hours. Preferably the reaction temperature is about 45° C. to about 110° C., more preferably at about 85° C. to about 100° C. for about 3 to 6 hours.

After completion of the dealkylation reaction, the resultant reaction mass may be cooled to ambient temperature, after removal of the solid bi-product salts that is produced, such as by filtration, the filtrate can be separated and isolate the tenofovir by any method known in the art, for example by solvent crystallization, solvent precipitation and the like. The tenofovir can be recovered by any conventional technique known in the art, for example filtration.

The resultant product may optionally be further dried. Drying can be suitably carried out in a tray dryer, vacuum oven, air oven, fluidized bed drier, spin flash dryer, flash dryer and the like. The drying can be carried out at a temperature ranging from about 60° C. to about 90° C. A high purity level of the resulting tenofovir, obtained by the aforementioned process, may have a chemical purity of at least about 97%, as measured by HPLC, preferably at least about 98%, as measured by HPLC and more preferably at least about 99%, as measured by HPLC.

The tenofovir recovered using the process of the present invention is having substantially free of Hypoxanthine impurity.

The present invention encompasses methods of preparing tenofovir and a pharmaceutically acceptable ester, or a salt thereof with high purity. The processes of the invention allow for economical synthesis, shorter reaction times, and yields of high purity.

The present invention provides pharmaceutically acceptable esters, or salts of tenofovir, obtained by a process comprising providing a tenofovir as obtained by the process described above, as a starting material or as an intermediate, where the yield and the purity of the pharmaceutically acceptable esters, or a salt thereof, preferably tenofovir disoproxil fumarate salt may have a purity equal to or greater than about 99.5% as determined by HPLC.

The present invention further provides a process for preparation of pharmaceutically acceptable esters, or a salt of tenofovir, preferably tenofovir disoproxil salts such as fumarate, phosphate, succinate; citrate, ferulate and the like.

The present invention further provides a process for preparation of pharmaceutically acceptable esters, or a salt of tenofovir, for instance tenofovir disoproxil fumarate, comprising:
  a) providing a tenofovir obtained by the processes described above in an organic solvent such as N-methyl pyrrolidinone and a base such as triethylamine,
  b) treating the resultant reaction mixture with chloromethyl isopropyl carbonate a temperature of about 50° C. to about 60° C. obtain tenofovir disoproxil, and
  c) saltification of the resultant tenofovir disoproxil with fumaric acid to obtain tenofovir disoproxil fumarate.

The present invention provides a tenofovir disoproxil fumarate, obtained by the process described herein, having a purity of at least about 97%, as measured by HPLC, preferably at least about 98% as measured by HPLC, and more preferably at least about 99.5%, as measured by HPLC; and substantially free of Hypoxanthine impurity of Formula:

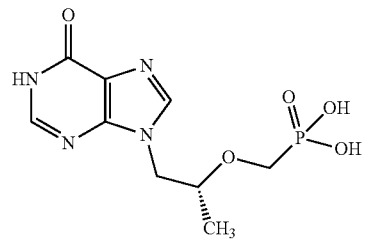

Hypoxanthine Impurity wherein the word "substantially free" refers to tenofovir disoproxil fumarate having less than about 0.2% of Hypoxanthine impurity, as measured by HPLC, more preferably less than about 0.1% of Hypoxanthine impurity, as measured by HPLC, still more preferably less than about 0.05% of Hypoxanthine impurity, as measured by HPLC.

As used herein, the term "isolated" refers to a chemical state well known among pharmaceutical chemists wherein the recited pharmaceutical ingredient has been separated from the medium in which it was created into a relatively pure physical state, before it is mixed with other pharmaceutical ingredients.

In one embodiment, the tenofovir disoproxil fumarate disclosed herein for use in the pharmaceutical compositions of the present invention can have a $D_{50}$ and $D_{90}$ particle size of less than about 400 microns, preferably less than about 200 microns, more preferably less than about 150 microns, still more preferably less than about 50 microns and most preferably less than about 15 microns. The particle sizes of the tenofovir disoproxil fumarate prepared according to the present invention can be obtained by any milling, grinding, micronizing, or other particle size reduction method known in the art to bring the solid state tenofovir disoproxil fumarate into any of the desired particle size range.

Advantages of the Invention

The present invention has the following advantages with respect to the reported literature, are:
i) avoids use of expensive and corrosive reagents like halotrimethylsilanes such as bromotrimethylsilane, chlorotrimethylsilane and iodotrimethylsilane for dealkylation of phosphonate esters for preparation of tenofovir thereby making the process economical and safe,
ii) avoids use of harsh acidic conditions like aqueous solutions of HCl or HBr for dealkylation of phosphonate esters for preparation of tenofovir thereby making the process free of undesired Hypoxanthine impurity,
iii) use of tedious workup procedures such as dimethyl formamide distillation at higher temperatures and accordingly formation of degradation impurities are avoided, making the process simple and cost effective, and
iv) avoids use of corrosive and concentrated acids as dealkylating agents to minimize the industrial effluent.

EXAMPLES

The following non limiting examples illustrate specific embodiments of the present invention. They are not intended to be limiting the scope of the present invention in any way.

Example 1

Preparation of Tenofovir Using Dimethyl Formamide-Hydrochloric Acid Complex

To a clean 3-necked 2 L round bottom flask equipped with a mechanical stirrer, thermometer socket and addition funnel dimethyl formamide (400 ml) and 9-[2-(R)-(hydroxy)propyl]adenine (HPA) (100 gms) were charged at temperature 20° C. to 35° C. Reaction mass was cooled to 0° C. to 5° C. and sodium amide (40.4 gms) was added at temperature 0° C. to −10° C. and stirred for 30 minutes at same temperature. Magnesium chloride (49.2 gms) was added and stirred for 1 hour at 25° C. to 30° C. To the reaction mass toluene (300 ml) was charged and heated to 75° C. to 80° C. Diethyl p-toluene sulfonyloxy methyl phosphonate (250 gms) (DESMP) was added and stirred for 2 hours at same temperature. Reaction mass was cooled to 0° C. to 5° C. and dry hydrochloric acid gas was passed for 5 hours. Reaction mass was heated to 90° C. to 95° C. and maintained for 3 hours. After completion of the dealkylation and monitored by HPLC, the solvent was removed completely under vacuum below 70° C. and water (400 ml) was added to the resultant residue at temperature 60° C. to 65° C. Filtered the salts formed and washed the salts with methylene chloride (300 ml). Filtrate was taken and methylene chloride layer was separated; then pH of the aqueous layer was adjusted to 2.5 to 3.0 with 50% sodium hydroxide solution at 20° C. to 30° C. Filtered the precipitated product and washed with water (100 ml) and then chilled acetone (100 ml). To the resultant wet product, water (900 ml) was charged and heated to 90° C. to 95° C. Temperature was cooled to 25° C. to 30° C. and filtered the product and washed with chilled water (50 ml) and then chilled acetone (100 ml). The wet product was dried at 70° C. to 75° C. under reduced pressure to provide the title compound.

Yield: 80 gms

HPLC purity: 99%

Example 2

Preparation of Tenofovir Using Dimethyl Formamide-Hydrochloric Acid Complex

To a clean 3-necked 2 L round bottom flask equipped with a mechanical stirrer, thermometer socket and addition funnel dimethyl formamide (200 ml), 9-[2-(R)-(hydroxy)propyl]adenine (HPA) (100 gms) and Magnesium t-butoxide (72 gms) were charged at temperature 20° C. to 35° C. and stirred for 30 minutes at same temperature. Diethyl p-toluene sulfonyloxy methyl phosphonate (225 gms) (DESMP) was added and temperature was raised to 75° C. to 80° C. and stirred for 2 hours at same temperature. Reaction mass was cooled to 0° C. to 5° C. and dry hydrochloric acid gas was passed for 5 hours. Reaction mass was heated to 90° C. to 95° C. and maintained for 4 hours. After completion of the dealkylation and monitored by HPLC, the solvent was removed completely under vacuum below 70° C. and water (400 ml) was added to the resultant residue at temperature 60° C. to 65° C. Adjusted pH of the reaction mass to about 1 with Concentrated HCl. Filtered the salts formed and washed the salts with 10% HCl solution. Filtrate was taken and pH was adjusted to about 2.5 with 50% NaOH solution and the reaction mass was cooled to 0° to 5° C. Filtered the precipitated product and washed with water (100 ml) and then washed with chilled acetone (100 ml). To the resultant wet product water (800 ml) was charged and heated to 90° C. to 95° C. Temperature was cooled to 25° C. to 30° C. and filtered the product and washed with chilled water (50 ml) and then washed with chilled acetone (100 ml). The wet product was dried at 70° C. to 75° C. under reduced pressure to provide the title compound.

Yield: 82 gms.

HPLC purity: 99.2%

Example 3

Preparation of Tenofovir Using Dimethyl Formarifide. HCl-Aluminium Chloride Complex To a clean 3-necked 2 L round bottom flask equipped with a mechanical stirrer, thermometer socket and addition funnel dimethyl formamide (200 ml) and 9-[2-(R)-(hydroxy)propyl]adenine (HPA) (50 gms) were charged at temperature 20° C. to 35° C. Reaction mass was cooled to 0° C. to 5° C. and sodium amide (20.2 gms) was added at temperature 0° C. to −10° C. and stirred for 30 minutes at same temperature. Magnesium chloride (24.6 gms) was added and stirred for 1 hour at 25° C. to 30° C. To the reaction mass toluene (150 ml) was charged and heated to 75° C. to 80° C. Diethyl p-toluene sulfonyloxy methyl phosphonate (125 gms) (DESMP) was added and stirred for 2 hours at same temperature. Reaction mass was cooled to 20° C. to 25° C. and acetic acid was added to obtain the phosphonate ester compound solution.

In another 3-necked 3 L round bottom flask dimethyl formamide-hydrochloric acid complex (150 ml) and aluminium chloride (138 gms) was added at 20° C. to 25° C. and heated to 100° C. and stirred for 15 minutes to obtain the dimethyl formamide-aluminium chloride complex. To the dimethyl formamide-aluminium chloride complex, phosphonate ester compound solution obtained above was added at temperature 95° C. and stirred for 5 hours at 90° C. to 95° C. After completion of the dealkylation, monitored by HPLC, the solvent was removed completely under vacuum below 70° C. and water (200 ml) was added to the resultant residue at temperature 60° C. to 65° C. Filtered the salts formed and washed the salts with methylene chloride (150 ml). Filtrate was taken and methylene chloride was separated then pH was adjusted the aqueous layer to 2.5 to 3 with 50% sodium hydroxide solution at 20° C. to 30° C. Filtered the precipitated product and washed with water (50 ml) and then washed with chilled acetone (50 ml). To the resultant wet product water (400 ml) was charged and heated to 90° C. to 95° C. Temperature was cooled to 25° C. to 30° C. and filtered the product and washed with chilled water (50 ml) and then washed with chilled acetone (100 ml). The wet product was dried at 70° C. to 75° C. under reduced pressure to provide the title compound.

Yield: 25 gms.

HPLC purity: 99.1%

Example 4

Preparation of Tenofovir Using Trimethylamine.HCl-Aluminium Chloride Complex To a clean 3-necked 2 L round bottom flask equipped with a mechanical stirrer, thermometer socket and addition funnel dimethyl formamide (200 ml) and 9-[2-(R)-(hydroxy)propyl] adenine (HPA) (50 gms) were charged at temperature 20° C. to 35° C. Reaction mass was cooled to 0° C. to 5° C. and sodium amide (20.2 gms) was added at temperature 0° C. to −10° C. and stirred for 30 minutes at same temperature. Magnesium chloride (24.6 gms) was added and stirred for 1 hour at 25° C. to 30° C. To the reaction mass toluene (150 ml) was charged and heated to 75° C. to 80° C. Diethyl p-toluene sulfonyloxy methyl phosphonate (125 gms) (DESMP) was added and stirred for 2 hours at same temperature. Reaction mass was cooled to 20° C. to 25° C. and acetic acid was added to obtain the phosphonate ester compound solution.

In another 3-necked 3 L round bottom flask trimethylamine. HCl (120 gms) and aluminium chloride (138 gms) were added at 20° C. to 25° C. and heated to 100° C. and stirred for 15 minutes to obtain the trimethylamine. HCl-aluminium chloride complex. To the trimethylamine. HCl-aluminium chloride complex, phosphonate ester compound solution obtained above was added at temperature 95° C. and stirred for 5 hours at 90° C. to 95° C. After completion of the dealkylation, monitored by HPLC, the solvent was removed completely under vacuum below 70° C. and water (200 ml) was added to the resultant residue at temperature 60° C. to 65° C. Filtered the salts formed and washed the salts with methylene chloride (150 ml). Filtrate was taken and methylene chloride was separated then pH was adjusted the aqueous layer to 2.5 to 3 with 50% sodium hydroxide solution at 20° C. to 30° C. Filtered the precipitated product and washed with water (50 ml) and then washed with chilled acetone (50 ml). To the resultant wet product water (400 ml) was charged and heated to 90° C. to 95° C. Temperature was cooled to 25° C. to 30° C. and filtered the product and washed with chilled water (50 ml) and then washed with chilled acetone (100 ml). The wet product was dried at 70° C. to 75° C. under reduced pressure to provide the title compound.

Yield: 30 gms.

HPLC purity: 98.9%.

Example 5-8

Tenofovir was prepared using different aluminium chloride-amine reagent using a procedure analogous to that employed in Example 4, as described in the following Table I:

TABLE I

| Ex | HPA (in gms) | sodium amide (in gms) | Magnesium chloride (in gms) | DESMP (in gms) | Amine | Aluminium chloride (in gms) | Yield (in gms) | Purity |
|---|---|---|---|---|---|---|---|---|
| 5 | 50 | 20.2 | 24.6 | 125 | Diisopropyl amine (104 gms) | 138 | 24 | 98.7% |
| 6 | 50 | 20.2 | 24.6 | 125 | Triethyl amine (109 gms) | 138 | 25 | 99.1% |
| 7 | 50 | 20.2 | 24.6 | 125 | Diethylamine (75.5 gms) | 138 | 23.5 | 98.8% |
| 8 | 50 | 20.2 | 24.6 | 125 | 2, 6 Lutidine (110.5 gms) | 138 | 20 | 98% |

Example 9

Preparation of Tenofovir Disoproxil Fumarate

To a clean 3-necked 1 L round bottom flask equipped with a mechanical stirrer, thermometer socket, addition funnel and dean-stark apparatus was charged cyclohexane (400 ml) and tenofovir (50 gms, obtained from example 1) and triethyl amine (34 gms) at temperature 20° C. to 35° C. Heated to 80° C. to 85° C. and stirred for 2 hours and simultaneously removed water liberated. The solvent was removed completely from the reaction mixture by distillation under vacuum at below 65° C. and to the obtained residue N-methyl pyrrolidinone (150 ml) and triethyl amine (34 gms) were charged at 25° C. to 30° C. Heated to 50° C. to 55° C. and chloromethyl isopropyl carbonate (125 gms) was added at same temperature and stirred for 4 hours. After completion of the reaction, the reaction mass was cooled to 20° C. to 25° C. and washed with cyclohexane (200 ml). Methylene chloride (500 ml) was charged into the organic layer and stirred for 1 hour at 10° C. to 15° C. Filtered the salts formed and washed the filtrate with water (500 ml), separated the layers and charged water (500 ml) to the organic layer. Adjusted pH to 6.5 to 7.5 with 10% ammonia solution and separated the organic layer from the aqueous layer. The solvent was removed from the organic layer under vacuum at below 35° C. to obtain oily product and then the oily product was diluted with isopropanol (150 ml).

In a clean another 3-necked 1 L round bottom flask equipped with a mechanical stirrer, thermometer socket and addition funnel was charged isopropanol (350 ml) and Fumaric acid (19 gms). Heated to 50° C. to 55° C. and stirred for 20 minutes and above obtained oily product solution was added at 50° C. to 55° C. Stirred for 30 minutes at this temperature and cooled to 0° C. to 5° C. Filtered the product and washed with chilled isopropanol (75 ml). The wet product was dried at 35° C. to 40° C. under reduced pressure to provide the title compound as crude (80 gms).

In another clean 3-necked 1 L round bottom flask equipped with a mechanical stirrer, thermometer socket and addition funnel was charged ethyl acetate (450 ml) and crude product (80 gms) at temperature 10° C. to 15° C. Stirred the slurry for 1 hour and filtered the product and washed with chilled ethyl acetate (50 ml). The wet product was dried at 35° C. to 40° C. for 6 hours under reduced pressure to provide the title compound.

Yield: 55 gms.
HPLC purity: 98.9%.

Comparative Example

Preparation of Tenofovir Using Aqueous HBr (U.S. Pat. No. 8,049,009)

To a clean 3-necked 2 L round bottom flask dimethyl formamide (200 ml) and 9-[2-(R)-(hydroxy)propyl]adenine (100 gms) were charged at temperature 25° C. to 35° C. and stirred for 5 minutes. Magnesium tert-butoxide (72 gms) was charged and heated to 60° C. Maintained for 1 hour at 60° C. to 65° C. and again heated to 75° C. Diethyl p-toluene sulfonyloxy methyl phosphonate (200 gms) (DESMP) was added in 2 hours time and stirred for 5 hours at 75° C. to 80° C. Reaction mass was cooled to 25° C. to 35° C. and acetic acid (60 gms) was added. Distill off the solvent completely under vacuum at below 80° C. to obtain the residue. To the residue, water (200 ml) and methylene chloride (1000 ml) were charged and filtered the salts formed and washed the salts with methylene chloride (3×200 ml). Filtrate was separated and aqueous layer was washed with methylene chloride (300 ml). Distill off the entire organic layer completely under vacuum up to 80° C. to obtain the tenofovir phosphonate diester residue. To the residue charged aqueous hydrobromic acid (470 ml) at 25° C. to 35° C. and heated to 95° C. and stirred for 5 hours at same temperature. The reaction mass was cooled to 25° C. to 35° C. and water (300 ml) was charged methylene chloride (300 ml) and stirred for 15 minutes. The methylene chloride layer was separated and adjusted the pH of aqueous layer to 2.5 to 3.0 with 50% NaOH solution at 25° C. to 30° C. Stirred for 4 hours at same temperature and cooled to 0° C. to 5° C. and stirred for 4 hours at same temperature. Precipitated product was filtered and washed with chilled water (100 ml) and then finally washed with chilled acetone (200 ml). The wet cake was dissolved in water (1000 ml) at temperature 95° C. to 100° C. The solution was cooled to 25° C. to 30° C. and then to 5° C. and stirred for 4 hours at 0° C. to 5° C. Precipitated product was filtered and washed with chilled water (50 ml) and chilled acetone (100 ml). The wet compound was dried at 70° C. to 75° C. under vacuum for 12 hours to obtain the title compound.

Yield: 68 gms.
HPLC purity: 98%.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for preparation of tenofovir comprising the step of dealkylating (R)-9-[2-(di-Alk-phosphonomethoxy)propyl]adenine of Formula

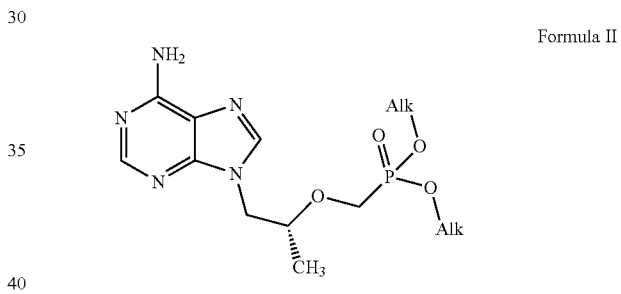

Formula II wherein Alk is independently a C1-4 alkyl, with a dealkylating ionic complex selected from the group consisting of a complex of amide and an acid, a complex of aluminum salt and an amide-acid reagent, and a complex of aluminum salt and an amine.

2. The process of claim 1, further comprising the step of converting the tenofovir into a tenofovir disoproxil or pharmaceutically acceptable salts thereof.

3. The process of claim 1, wherein Alk is independently selected from the group consisting of methyl, ethyl, propyl, butyl, isopropyl, isobutyl, and combinations thereof.

4. The process of claim 1, wherein the dealkylating ionic complex is a complex of an amide and an acid.

5. The process of claim 4, wherein the amide is selected from the group comprised of dimethyl formamide, dimethyl acetamide, formamide, N-methyl formamide, methyl formamide, 2-pyrrolidone, N-Methyl-2-pyrrolidone, N-vinyl pyrrolidone, and combinations thereof; and the acid is selected form the group comprised of hydrochloric acid, hydrobromic acid, orthophosphoric acid, sulfuric acid, and combinations thereof.

6. The process of claim 4, wherein the dealkylating ionic complex is a complex of dimethyl formamide and hydrochloric acid.

7. The process of claim 4, wherein the molar ratio of the amide to the acid is between about 1:0.5 and about 1:3.

8. The process of claim 1, wherein the suitable dealkylating ionic complex is a complex of aluminum salt and an amide-acid reagent.

9. The process of claim 8, wherein the aluminum salt is selected from the group consisting of aluminum chloride, aluminum bromide aluminum iodide, and combinations thereof; and the amide-acid reagent comprises a complex of an amide and an acid.

10. The process of claim 9, wherein the amide in the amide-acid complex is selected from the group consisting of dimethyl formamide, dimethyl acetamide, formamide, N-methyl formamide, methyl formamide, 2-pyrrolidone, N-Methyl-2-pyrrolidone, N-vinyl pyrrolidone, and combinations hereof; and the acid in the amide-acid complex is selected from the group consisting of hydrochloric acid, hydrobromic acid, orthophosphoric acid, sulfuric acid, and combinations thereof.

11. The process of claim 9, wherein the complex of amide and an acid is a complex of dimethyl form amide and hydrochloric acid.

12. The process of claim 8, wherein the complex of an aluminum salt and an amide-ac id reagent is a complex of aluminum chloride, dimethyl formamide, hydrochloric acid, and combinations thereof.

13. The process of claim 1, wherein the suitable dealkylating ionic complex is a complex of an aluminum salt and an amine.

14. The process of claim 13, wherein
a) the aluminum salt is selected from the group consisting of aluminum chloride, aluminum bromide aluminum iodide, and combinations thereof; and
b) the amine is selected from the group consisting of a compound of formula $(R)_2NH$, wherein R is independently a linear or branched $C_1$-$C_4$ alkyl group, a linear or branched $C_2$-$C_6$ alkenyl group, a $C_3$-$C_7$ cycloalkyl group, an aryl group, or an aralkyl group; or
a compound of Formula NRaRbRc, in which Ra, Rh and Rc is independently hydrogen, an aryl group, a linear or branched $C_1$-$C_4$ alkyl group, or Ra, Rb or Rc may form a cyclic ring with the nitrogen.

15. The process of claim 14, wherein
the linear or branched $C_1$-$C_4$ alkyl is selected from the group consisting of methyl, ethyl, propyl, isopropyl, butyl, isobutyl, sec-butyl and tert-butyl, and combinations thereof;
the linear or branched alkenyl is selected from the group consisting of an ethenyl or vinyl, propenyl or allyl, 1-propenyl, n-butenyl, isobutenyl, 3-methylbut-2-enyl, n-pentenyl or hexenyl, and combinations thereof;
the C3-C7cycloalkyl is selected from the group consisting of cyclopropyl, cyclohexyl, and combinations thereof;
the aryl is selected from the group consisting of phenyl, naphthyl and combinations thereof; or
the aralkyl is selected from the group consisting of benzyl, 1-phenylethyl, and combinations thereof.

16. The process of claim 14, wherein the amine is selected from the group consisting of diethylamine, diisopropyl amine, di-n-propylamine, diallylamine, diphenylamine, dibenzylamine, trimethylamine, triethylamine, tripropylamine, tributylamine, N,N-dimethylethylamine, N,N-diethylmethylamine, N,N-dimethylbutylamine, N,N-dimethylaniline, N,N-diethylaniline, N-methyl-N-ethyl aniline, N-methyl-N-isopropyl aniline, 1-N,N-dimethylnaphthalene, 2-N,N-dimethyl naphthalene, dicyclopropylamine, dicyclohexylamine, pyridine, 2,6-lutidine, and combinations thereof.

17. The process of claim 14, wherein the amine is in the form of a free amine or an acceptable salt thereof.

18. The process of claim 13, wherein the complex of aluminum salt and an amine is selected from the group comprised of aluminum chloride-trimethylamine, HCl, aluminum chloride-diisopropylamine, aluminium chloride-diethylamine and aluminium chloride-2,6-lutidine, and combinations thereof.

19. The process of claim 1, wherein the dealkylating step is carried out in a suitable solvent selected from the group consisting of amides and of sulfoxides.

20. The process of claim 19, wherein the suitable solvent is dimethyl formamide, dimethyl acetamide, form amide, N-methyl formamide, methyl formamide, 2-pyrrolidone, N-Methyl-2-pyrrolidone, N-vinyl pyrrolidone, dimethyl sulfoxide; and combinations thereof.

* * * * *